United States Patent [19]
Daftary

[11] Patent Number: 5,362,235
[45] Date of Patent: Nov. 8, 1994

[54] ANATOMICAL RESTORATION DENTAL IMPLANT SYSTEM WITH INTERLOCKABLE ANGLED ABUTMENT ASSEMBLY

[76] Inventor: Fereidoun Daftary, 50 N. La Cienega Blvd., Beverly Hills, Calif. 90211

[21] Appl. No.: 157,658

[22] Filed: Nov. 26, 1993

Related U.S. Application Data

[63] Continuation-in-part of Ser. No. 61,746, May 17, 1993, Pat. No. 5,297,963.

[51] Int. Cl.⁵ .................. A61C 13/12; A61C 13/225; A61C 8/00
[52] U.S. Cl. .................... 433/172; 433/173; 433/174
[58] Field of Search ............... 433/172, 173, 174, 175, 433/176

[56] References Cited

U.S. PATENT DOCUMENTS

| | | | |
|---|---|---|---|
| 4,850,870 | 7/1989 | Cazzara et al. | 433/174 |
| 5,035,619 | 7/1991 | Daftary | 433/173 |
| 5,040,983 | 8/1991 | Binon | 433/174 X |
| 5,071,351 | 12/1991 | Green, Jr. et al. | 433/173 |
| 5,073,111 | 12/1991 | Daftary | 433/173 |
| 5,104,318 | 4/1992 | Riche et al. | 433/173 X |
| 5,116,225 | 5/1992 | Riera | 433/173 |
| 5,135,395 | 8/1992 | Marlin | 433/174 |
| 5,145,372 | 9/1992 | Daftary et al. | 433/173 |
| 5,209,659 | 5/1993 | Friedman et al. | 433/173 |

*Primary Examiner*—Gene Mancene
*Assistant Examiner*—Nicholas D. Lucchesi
*Attorney, Agent, or Firm*—Thomas I. Rozsa; Tony D. Chen

[57] ABSTRACT

The present invention is an anatomical restoration dental implant system with an interlockable angled abutment assembly. The angled abutment assembly includes a screw member, an angled abutment member and a bolt member. The bolt member has a hexagonal head segment and an elongated shaft segment with screw threads for securing a healing cap to an implant fixture and connecting the angled abutment member. The angled abutment member has a continuous frusto-conical shaped divergent body with a smaller distal end, a larger proximal end and a stepped interior bore extending through the proximal end along an axis offset from an axis of the divergent body. The stepped interior bore has a narrow cylindrical section and a 12-side polygonal section. The angled abutment member can be mounted on the healing cap by engaging the head segment of the bolt member with the 12-side polygonal section of the interior bore of the angled abutment member, which allows the angular orientation of the angled abutment member to be adjustable in any 30 degree interval, and the screw member can be used to secure the angled abutment member to the bolt member.

13 Claims, 6 Drawing Sheets

ANATOMICAL RESTORATION DENTAL IMPLANT SYSTEM WITH INTERLOCKABLE ANGLED ABUTMENT ASSEMBLY

This application is a continuation-in-part of patent application Ser. No. 08/061,746 filed May 17, 1993 (hereafter "the '746 application"), now U.S. Pat. No. 5,297,963.

BACKGROUND OF THE INVENTION

1. Field of the Invention

The present invention relates generally to the field of dental implants and in particular to a system providing a tooth analogue and a gingival tissue healing cap which results in a restoration having tissue-implant profiles similar to that of a natural tooth and its surrounding gingiva. The present invention also relates to fitting a tooth with a temporary crown and final prosthesis after the initial implant structure has been inserted and the surrounding tissue has healed. More particularly, the present invention relates to the field of anatomical restoration dental implant systems with interlockable elliptical healing cap and abutment.

2. Description of the Prior Art

Many systems have been proposed for rigidly fixing metal or ceramic materials to the alveolus of a human mandible or maxilla in an effort to provide a long term replacement for lost teeth. Early systems were successful for only limited periods of time and were eventually rejected as foreign bodies. Later systems, as described by U.S. Pat. Nos. 3,589,011 to Sneer, 3,797,113 to Brainin, 3,979,828 to Taylor, 4,324,550 to Reuther et al., and 4,416,679 to Mozsary et al., have proven to offer long term success by providing rigid anchorage in the supporting bone. Intraoral restoration of such ossointegrated devices has been accomplished with many different systems that modified the original attempts. Such modifications have been described in U.S. Pate. Nos. 4,780,080 to Harras, 4,713,003 to Symington et al., and 4,657,510 to Gittlemen. However, these restorative systems have required biologic and aesthetic compromises. The interface between an implant and its surrounding gingival tissue is often insufficiently close to prevent food and bacteria from entering this area. Such foreign matter can cause chronic infection and bone loss, resulting in eventual loss of the implant. Implants in current use have a round root form dimensionally different from that of a normal tooth root morphology. This makes aesthetic restoration difficult and impedes the development of a natural soft gingival tissue contour.

The inventor and applicant of the present invention has been practicing anatomical restoration dental implant surgery for many years and is the patentee of a series of U.S. patents related to anatomical restoration dental implant systems. U.S. Pat. No. 5,073,111 issued to Daftary on Dec. 17, 1991 (hereafter "the '111 patent") disclosed an anatomical restoration dental implant system. Shown in FIGS. 1 and 2, the '111 patent disclosed an anatomical restoration dental implant system for implanting a tooth analogue 102 in the alveolus of the jawbone 104. The system comprises an implantable fixture 106 implanted through opened gingival tissue 108 into the alveolus of the jaw bone 104. A cover screw (not shown) is used for sealing the hollow of the implant fixture 106 during the time the jaw bone 104 is growing about the implant fixture 106. After osseointegration of the implant fixture 106, the gingiva 108 is reopened and the cover screw is removed and replaced by a healing cap 110. The healing cap 110 provides a predetermined contour to the re-healing gingival tissue 108. After the re-opened gingival tissue 108 has healed about the healing cap 110, the healing cap 110 is removed and replaced with an abutment 112 having the same contour as that of the healing cap 110. Having the same contour permits the abutment 112 to tightly fit the healed opening in the gingival tissue 108 upon engagement of the abutment 112 with the implant fixture 106. The abutment 112 is removably affixed to the implant fixture 106 by a screw 114. Thereafter the tooth analogue 102 is releasibly engagable with the abutment 112 by a small holding screw 116.

U.S. Pat. No. 5,035,619 issued to Daftary on Jul. 30, 1991 (hereafter "the '619 patent") disclosed an anatomical restoration dental implant system with improved healing cap and abutment. U.S. Pat. No. 5,145,372 issued to Daftary et al. on Sep. 8, 1992 (hereafter "the '372 patent") disclosed an anatomical restoration dental implant system with reinforced healing cap and abutment. The '619 patent introduced an assembly of a two-piece healing cap and a matching abutment for improving the healing process of the gingival tissue 108, and the '372 patent provided a reinforced assembly of the two-piece healing cap and the matching abutment. The two-piece healing cap configurations are designed to prevent the unnecessary damage or delay to the healing of the gingival tissues. However, it is always desirable to improve the anatomical restoration dental implant system so that it can provide a contour more nearly approximating that of a natural tooth and its surrounding tissue, and an implant root and gingival tissue interface that enhances the resistance to bacterial infection.

In addition, under some special circumstances an angled abutment member is needed for supporting a tooth analogue. A typical one of these special circumstances is that the part of a patient's jaw bone directly underneath the tooth is damaged, so that the dental implant fixture has to be implanted on an adjacent part of the patient's jaw bone. Under such a circumstance, the exposed surface of the dental implant fixture is often misaligned. After a healing cap is secured to the implant fixture, the axis normal to the top surface of the healing cap is often not aligned with the axis of the tooth. In this situation, an angled abutment member is needed. Therefore, it is also desirable to have an angled abutment assembly which can support a tooth analogue on the healing cap in such misaligned situation.

SUMMARY OF THE INVENTION

The present invention is an anatomical restoration dental implant system with an interlockable angled abutment assembly.

Figure 3:
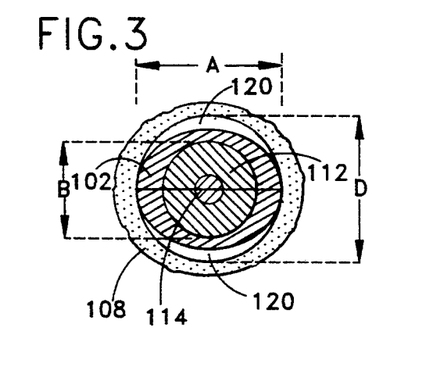
FIG. 3 is a cross-sectional view taken along line 3—3 in FIG. 2.
Figure 4:
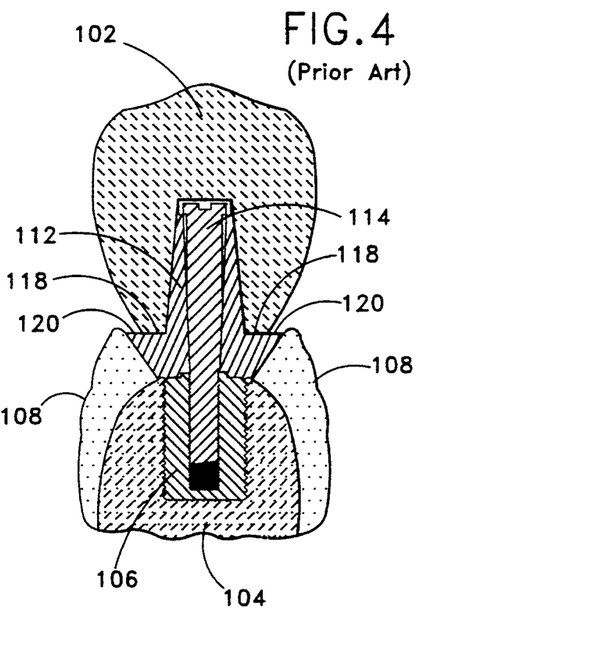
FIG. 4 is another cross-sectional view of the prior art anatomical restoration dental implant system, observed at a 90 degree angle from that of FIG. 3, showing that two opposite narrow spaces are left between the tooth analogue and the gingival tissues because of the mismatching between the elliptical root of the tooth analogue and the circular shoulder around the abutment.

It is known that one of the common features of all existing anatomical restoration dental implant systems, including the '111 patent, the '619 Patent and the '372 patent, is that once the abutment 112 is in place, it provides a circular shoulder 118 around the abutment 112 for a tooth analogue 102. In practicing anatomical restoration dental implant surgeries, the inventor of the present invention has discovered that, when the root of the tooth analogue is oval or elliptical instead of round or circular, it will not match perfectly with the circular shoulder around the abutment. As shown in FIG. 3, when the bottom end or root of the tooth analogue 102 is elliptical, it will not fully cover the circular shoulder 118. In other words, the bottom end surface of the tooth analogue 102 is often not a perfect circle but an ellipse. While the diameter A of the long-axis of the ellipse is matching the diameter D of the circular shoulder 118, the diameter B of the short-axis of the ellipse is not. The result of this mismatching is shown in FIG. 4, which is observed at a 90 degree angle from that of FIG. 3. As shown in FIGS. 3 and 4, there will be two opposite narrow spaces 120 left between the tooth analogue 102 and the gingival tissues 108. This creates a serious problem because it will take a long period of time for the gingival tissues 108 to recover and heal around the tooth analogue 102 to fill the two narrow spaces, and meanwhile food debris and bacteria may be collected within the spaces, which in turn will impede the complete healing of the gingival tissues and increases the chance of causing infectious diseases.

Figure 5:
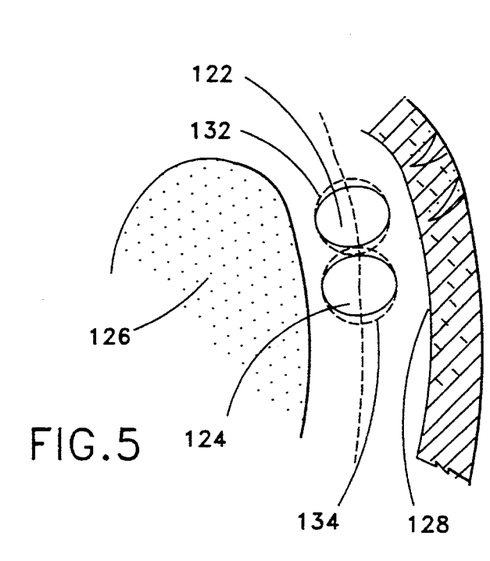
FIG. 5 is an illustrative diagram of a patient's oral cavity, showing the prior art anatomical restoration dental implant system with circular shoulder around the abutment, which may interfere with an adjacent anatomical restoration dental implant system and prevent two tooth analogues from being positioned closely as desired.

Another problem presented by the mismatch is shown in FIG. 5, which is an illustrative diagram of a patient's oral cavity. Suppose two tooth analogues 122 and 124 are going to be positioned next to each other between the patient's tongue 126 and the interior surface 128 of the patient's cheek. The profile of the bottom surface of the tooth analogues is elliptical. According to the orientation of the natural tooth, the long-axis of the ellipse is aligned with the general radius direction of the patient's oval cavity. Dotted circle 132 shows the profile of the circular shoulder around the abutment for supporting tooth analogue 122, and dotted circle 134 shows the profile of the circular shoulder around the abutment for supporting tooth analogue 124. It can be seen that the larger profile of the circular shoulders will prevent the two tooth analogues 122 and 124 from being positioned at a desired or required close distance because the circular shoulders around the abutments for supporting the two tooth analogues 122 and 124 will interfere with each other.

It has been discovered, according to the present invention, that if a new healing cap with oral or elliptical shaped top surface is utilized with the abutment, then the shoulder around the abutment is elliptical which will perfectly match with the oval root of the tooth analogue. Therefore, it is a primary object of the present invention to provide a healing cap with an elliptical top surface for providing an elliptical shoulder around the abutment, so that there can be a perfect match between the elliptical root of a tooth analogue and the abutment shoulder.

Figure 1:
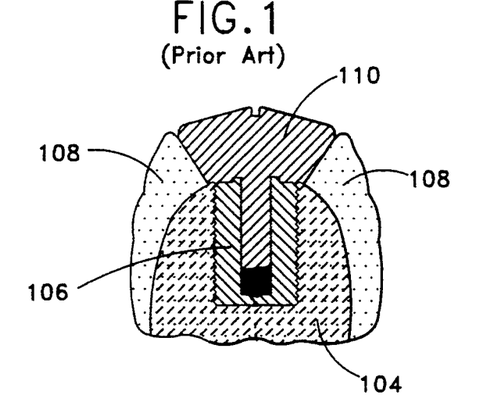
FIG. 1 is a cross-sectional view of a prior art anatomical restoration dental implant system as disclosed in the '111 patent, showing a healing cap which is threaded onto the implant fixture.
Figure 2:
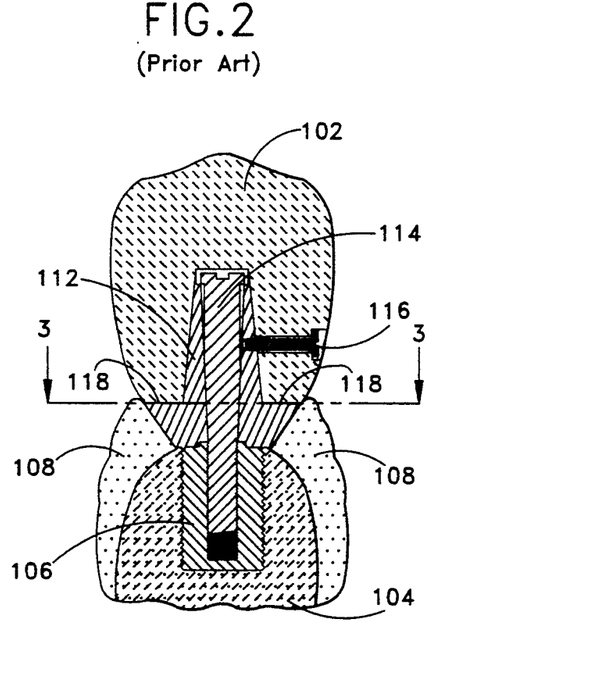
FIG. 2 is also a cross-sectional view of the prior art anatomical restoration dental implant system as disclosed in the '111 patent, showing an abutment which is threaded onto the implant fixture for supporting a tooth analogue.

As shown in FIG. 1, in the prior art when the top of the healing cap 110 is round, it does not matter how it is oriented. Thus the healing cap 110 can be simply threaded to the implant fixture 106 until they are fully engaged. However, for the new healing cap with elliptical top, it must be oriented in the way shown in FIG. 5, that is, the long-axis of the ellipse must be aligned with the general radius direction of the patient's oval cavity. Consequently the new healing cap must have no threaded relationship with the implant fixture 106. In other words, the angle of the new healing cap must be adjustable when it is attached to the implant fixture 106.

Therefore, it is also an object of the present invention to provide a separate bolt for securing the new elliptical healing cap to the implant fixture which allows the adjustment of the orientation of the elliptical healing cap. Accordingly, the present invention is an anatomical restoration dental implant system with an elliptical healing cap assembly and matching abutment member. The present invention elliptical healing cap assembly includes an elliptical healing cap member and a separate bolt member. The bolt member extends through a central bore of the healing cap member, and has screw threads so that it can be threadedly engaged with the implant fixture to tightly secure the elliptical healing cap member to the implant fixture.

It has been discovered, according to the present invention, that it will be desirable to make the healing cap and the bolt not only separable, but also interlockable. Making the two pieces of the healing cap assembly interlockable can prevent mismatching the pieces of different healing caps, ease the effort of aligning the two pieces in a patient's oral cavity, and reduce the chance of losing the small bolt in the patient's oral cavity.

It has also been discovered, according to the present invention, that if instead of having a smooth bore, the healing cap member of the elliptical healing cap assembly has a central bore with screw threads, then when the bolt member of the of the elliptical healing cap assembly is extended through the central bore of the healing cap member, the bolt member can be threadedly engaged with the healing cap member so that they are interlocked with each other.

However, it has further been discovered, according to the present invention, that if the bolt member is threadedly engaged with both the healing cap member and the implant fixture, then the threaded relationship between the healing cap member and the bolt member will prevent the adjustment of the orientation of the healing cap member when the bolt member is tightened to the implant fixture. This is because there are three interconnections or cross-engagements between the three pieces, i.e., the healing cap member, the bolt member and the implant fixture. The bolt member is threadedly engaged with both the healing cap member and the implant fixture. On the one hand, when the bolt member has a threaded relationship with the healing cap member, it applies not only a translational downward force but also a rotational torque to the healing cap member. The translational force will act to fasten the healing cap to the implant fixture, but the rotational torque will act to rotate the healing cap about the implant fixture. Therefore, if the bolt member is simultaneously threadedly engaged with both the implant fixture and the healing cap member, then the latter engagement will act to change the orientation of the elliptical healing cap member. This is impermissible because the orientation of the elliptical healing cap must be kept unchanged, so that the long-axis of the elliptical healing cap member is aligned with the general radius direction of the patient's oral cavity.

It has additionally been discovered, according to the present invention, that if the bolt member is divided into two sections including an upper smooth section and a lower threaded section, and alternatively the central bore of the healing cap member is divided into two sections including an upper threaded section and a lower smooth section which are opposite to two sections of the bolt member, then when the bolt member is initially extended into the central bore of the healing cap member from the upper end of the healing cap member, the lower threaded section of the bolt member will threadedly engage with the upper threaded section of the healing cap member. However, when the bolt member is further extended into the central bore of the healing cap member, the lower threaded section of the bolt member will disengage from the upper threaded section of the healing cap member and align with the lower smooth section of the healing cap member, and there will no longer be a threaded relationship between the bolt member and the healing cap member because their respective threaded portions are offset from each other. Therefore, since the bolt member is threadedly engaged with the implant fixture and it is no longer threadedly engaged with the coping member, there is no action or force from the bolt member to rotate the healing cap member. Thereafter the lower threaded section of the bolt member can be threaded into the fixture to secure the healing cap thereon.

It has also been discovered, according to the present invention, that if the matching abutment member has a lower bolt portion which is identical to the bolt member of the elliptical healing cap assembly, then it can be attached to the healing cap member by simply replacing the bolt member, and the attachment of the abutment member will not have any effect on the orientation of the healing cap member because when the abutment member is threadedly engaged with the implant fixture, it is no longer threadedly engaged with the healing cap member.

It is therefore another primary object of the present invention to provide an interlockable elliptical healing cap assembly for anatomical restorative dental implant systems. The interlockable feature of the present invention healing cap assembly will prevent the pieces of different healing caps from being mismatched, ease the difficulty of alignment of the two pieces in a patient's oral cavity, and reduce the chance of dropping the bolt member into the patient's oral cavity.

It is also an object of the present invention to provide an interlockable elliptical healing cap assembly for anatomical restorative dental implant systems, where the central bore of the healing cap member has inner screw threads engagable with the outer screw threads of the bolt member, so that the healing cap member and the bolt member can be threadedly engaged and thereby interlocked.

It is a further object of the present invention to provide an interlockable elliptical healing cap assembly for anatomical restorative dental implant systems, where the healing cap member is only threadedly engaged with the bolt member when the bolt member has not yet threadedly engaged with the implant fixture. When the bolt member is threadedly engaged with the implant fixture, the healing cap member is no longer threadedly engaged with the bolt member to allow the adjustment of the orientation of the healing cap member.

It is an additional object of the present invention to provide an interlockable elliptical healing cap assembly for anatomical restorative dental implant systems, where the bolt member has an upper smooth section and a lower threaded section, and the central bore of the healing cap member has alternatively an upper threaded section and a lower smooth section. This design offsets the threaded portions of the two interlockable members.

When the bolt member is initially extended into the central bore of the healing cap member from the upper end of the healing cap member, the lower threaded section of the bolt member will threadedly engage with the upper threaded section of the healing cap member. When the bolt member is further extended into the central bore of the healing cap member, the lower threaded section of the bolt member will disengage from the upper threaded section of the healing cap member and align with the lower smooth section of the healing cap member, and there will no longer be a threaded relationship between the bolt member and the healing cap member because their respective threaded portions are offset from each other. Therefore, since the bolt member is threadedly engaged with the implant fixture and it is no longer threadedly engaged with the coping member, there is no action or force from the bolt member to rotate the healing cap member. Thereafter the lower threaded section of the bolt member can be threaded into the fixture to secure the healing cap thereupon.

It is another object of the present invention to provide a matching abutment member having a lower bolt portion that is identical to the bolt member of the elliptical healing cap assembly, so that it can be attached to the healing cap member by simply replacing the bolt member without altering the orientation of the healing cap member, since once the abutment member is threadedly engaged with the implant fixture, it is no longer threadedly engaged with the healing cap member.

Described generally, the present invention is an interlockable elliptical healing cap assembly attachable to an anatomical restoration dental implant fixture which is embedded into a patient's jawbone and has an exposed end having a hollow portion with inner screw threads. The healing cap assembly includes an integral bolt member which has a widened head segment and an elongated shaft segment, where the shaft segment has a proximal section with screw threads and a smooth distal section. The healing cap assembly further includes a healing cap member which has a divergent body with a smaller proximal end, a larger distal end, and a stepped interior bore extending from the distal end to the proximal end, where the larger distal end is elliptical shaped and has a long-axis and a short axis, and the interior bore has a smooth proximal section and a threaded distal section. The healing cap member and the bolt member are interlockable by threading the proximal section of the shaft segment of the bolt member into the distal section of the interior bore of the healing cap member. The present invention also comprises a matching abutment member for supporting a tooth analogue with an elliptical root. The abutment member has a proximal bolt segment which is identical to the bolt member of the healing cap assembly, and a distal frusto-conical shaped head segment which has a larger proximal end integrally connected to the proximal bolt segment, and a smaller distal end with means for adapting a driving tool. The large proximal end of the abutment member is circular shaped and has a diameter smaller than the short-axis of the elliptical shaped distal end of the healing cap member, such that when the abutment member is attached to the healing cap member in replacement of the bolt member for supporting the tooth analogue, an elliptical shoulder is created for matching the elliptical root of the tooth analogue.

In addition, it has been further discovered, according to the present invention, that under some special circumstances an angled abutment member is needed for supporting a tooth analogue. A typical one of these special circumstances is that the part of a patient's jaw bone directly underneath the tooth is damaged, so that the dental implant fixture has to be implanted on an adjacent part of the patient's jaw bone. Under such a circumstance, the exposed surface of the dental implant fixture is often misaligned. In other words, the axis normal to the exposed surface of the implant fixture is often not aligned with the axis of the tooth. In this situation, an angled abutment member is needed.

When an angled abutment member is used, its angular direction must be correctly aligned with the axis of the tooth analogue. It is often done by having an anti-rotational engagement between the healing cap and the angled abutment member, such as a hexagonal or polygonal mating. The angled abutment member can be connected to the healing cap through a bolt member, and fastened thereon by a screw member. The bolt member is similar to the bolt member of the interlockable healing cap assembly, i.e., the bolt member of the angled abutment assembly can also interlockably engage with the healing cap.

Therefore it is an additional object of the present invention to provide an angled abutment assembly which includes an angled abutment member, a bolt member and a screw member. The bolt member is identical to the bolt member of the previously discussed interlockable healing cap assembly, so it can be interlockably engaged with the healing cap, except the head portion of the bolt member is modified to facilitate the connection with the angled abutment member.

Described generally, the present invention also includes an angled abutment assembly attachable to a healing cap mounted on an anatomical restoration dental implant fixture, which is embedded into a patient's jawbone and has an exposed end having a hollow portion with inner screw threads, for supporting a tooth analogue along a direction offset from an axis of the fixture. The angled abutment assembly includes a screw member, an angled abutment member and a bolt member. The screw member has a widened head segment and a shaft segment with a threaded proximal section. The angled abutment member has a distal divergent portion and a proximal base portion integrally connected together; the divergent portion having a smaller distal end and the base portion having a larger proximal end. The angled abutment member further has an interior bore extending from the proximal end of the base portion to the divergent portion along an axis perpendicular to the proximal end of the base portion and offset from an axis of the divergent portion, the interior bore having a narrow cylindrical distal section and a wide polygonal proximal section. The bolt member has a hexagonal head segment and an elongated shaft segment with a threaded proximal section. The head segment has a top screw hole. The bolt member can be used to secure the healing cap to the implant fixture. The angled abutment member can be mounted on the healing cap by engaging the head segment of the bolt member with the polygonal proximal section of the interior bore of the angled abutment member, which allows the angular orientation of the angled abutment member to be adjustable, and the screw member can be used to secure the angled abutment member to the bolt member.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figures 6, 7, 8, 9, 10:
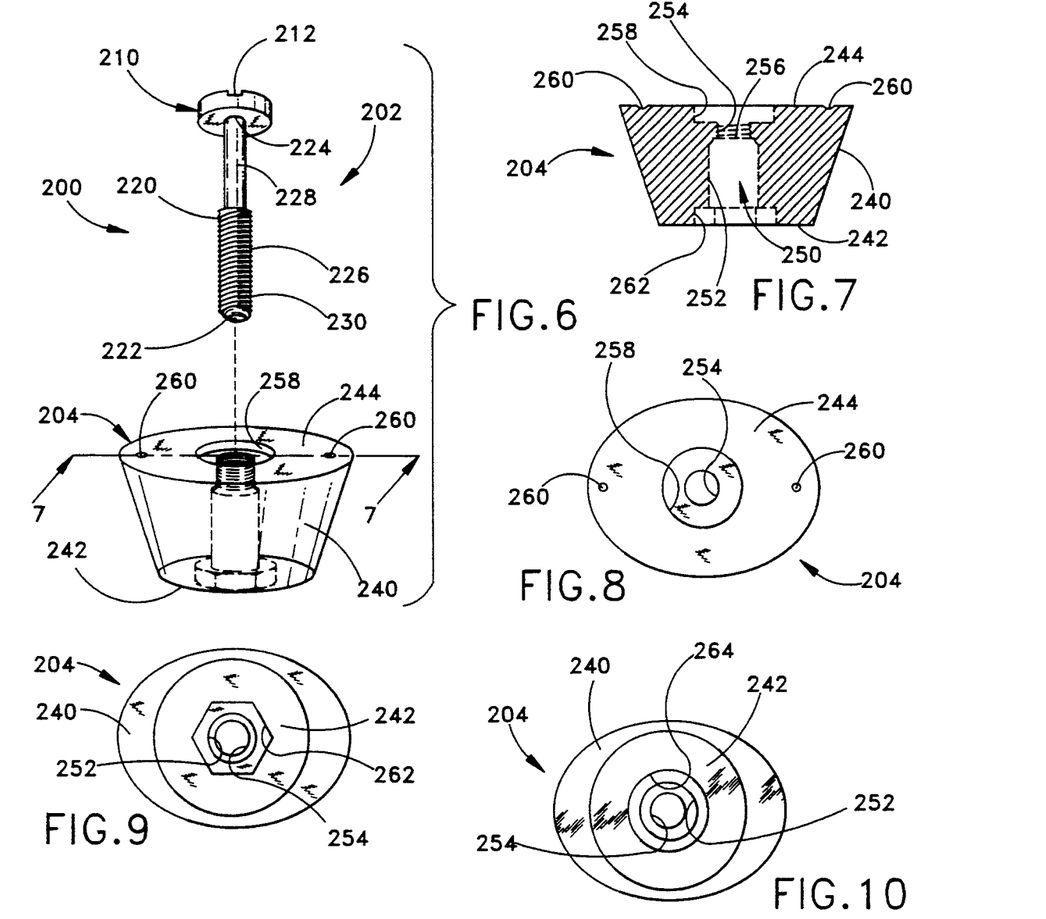
FIG. 6 is a perspective view of the present invention interlockable elliptical healing cap assembly, including an elliptical healing cap member and a bolt member.
FIG. 7 is a cross-sectional view of the elliptical healing cap member of the present invention interlockable elliptical healing cap assembly.
FIG. 8 is a top view of the elliptical healing cap member of the present invention interlockable elliptical healing cap assembly.
FIG. 9 is a bottom view of the elliptical healing cap member of the present invention interlockable elliptical healing cap assembly, showing a hexagonal recess for matching with a complementary hexagonal lip on the implant fixture.
FIG. 10 is a bottom view of an alternative embodiment of the elliptical healing cap member of the present invention interlockable elliptical healing cap assembly, showing a round recess for matching with a complementary circular lip on the implant fixture.

Referring to FIG. 6, there is shown a perspective view of the present invention healing cap assembly 200, including a bolt member 202 and an elliptical healing cap member 204. The bolt member 202 and the elliptical healing cap member 204 are interlockable.

Referring now to FIG. 6, there is illustrated a perspective view of the bolt member 202. The bolt member 202 has a widened head segment 210 and an elongated shaft segment 220. The widened head segment 210 is disc shaped with a top notch 212 to accommodate a driving tool such as a screw driver for rotating the bolt member 202. The shaft segment 220 has a proximal end 222 and a distal end 224, where the head segment 210 is integrally connected to the distal end 224 of the shaft segment 220. The shaft segment 220 further includes a proximal section 226 and a distal section 228. The proximal section 226 has outer screw threads 230 which are compatible with the inner screw threads of the hollow portion of the implant fixture, whereas the distal section 228 is smooth and has no screw threads.

Referring now to FIGS. 6, 7 and 8, where FIG. 6 is a perspective view of the elliptical healing cap member 204, FIG. 7 is a cross-sectional view of the elliptical healing cap member 204, and FIG. 8 is a top view of the elliptical healing cap member 204. The healing cap member 204 has a divergent body 240 which has a smaller proximal end 242 and a larger distal end 244. The smaller proximal end 242 is circular shaped, whereas the larger distal end 244 is elliptical shaped and has a long-axis and a short axis. The healing cap member 204 further has a stepped interior bore 250 extending from the distal end 244 to the proximal end 242. The interior bore 250 has a wider proximal section 252 and a narrower distal section 254. The proximal section 252 is smooth, whereas the distal section 254 has inner screw threads 256 which are compatible with the outer screw threads 230 of the proximal section 226 of the shaft segment 220 of the bolt member 202. The interior bore 250 is further widened at the larger distal end 244 of the healing cap member 204 to form a circular socket 258 for receiving the disc shaped head segment 210 of the bolt member 202, such that the head segment 210 of the bolt member 202 is flush with the large distal end 244 when it is seated within the circular socket 258. In addition, on the large distal end 244 of the healing cap member 204, two small indents 260 arc provided to accommodate the small tips of a dental tool such as a forceps for orienting the healing cap member 204.

FIGS. 9 and 10 are bottom views of the elliptical healing cap 204 showing the interference feature at the small distal end 242 of the elliptical healing cap 204. At the exposed end of the dental implant fixture, there is typically a slightly raised circumferential lip for facilitating the coupling with other dental components such as a cover screw, an impression coping or a healing cap. The circumferential lip is often hexagonal or circular shaped. FIG. 9 shows one embodiment of the present invention healing cap member 204, where a hexagonal recess 262 is provided at the small proximal end 242 of the healing cap member 204 for matching a complementary hexagonal lip at the exposed end of the dental implant fixture. FIG. 10 shows an alternative embodiment of the present invention healing cap member 204, where a circular recess 264 is provided at the small proximal end 242 of the healing cap member 204 for matching a complementary circular lip at the exposed end of the dental implant fixture.

Figure 11:
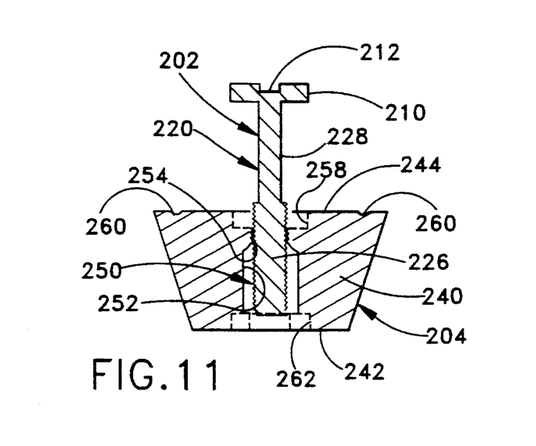
FIG. 11 is a cross-sectional view showing the interlockable feature of the elliptical healing cap member and the bolt member of the present invention interlockable elliptical healing cap assembly.

Referring to FIG. 11, there is shown the interlockable feature of the elliptical healing cap member 204 and the bolt member 202 of the ;present invention interlockable elliptical healing cap assembly 200. The healing cap member 204 and the bolt member 202 are interlockable by threading the proximal section 226 of the shaft segment 210 of the bolt member 202 into the distal section 254 of the interior bore 250 of the healing cap member 204, since the outer screw threads 230 at the proximal section 226 of the shaft segment 210 of the bolt member 202 are compatible with the inner screw threads 256 at the distal section 254 of the interior bore 250 of the healing cap member 204.

This interlockable feature is a critical advantage of the present invention healing cap assembly over the prior art healing cap assemblies. By having the bolt member 202 and the healing cap member 204 interlocked, the present invention healing cap assembly 200 can be handled together as a unit, which reduces the possibility of either dropping or losing the small bolt member 202 into the patient's oral cavity. It also makes the effort of aligning the bolt member 202 and the healing cap member 204 in a patient's oral cavity easier. It further reduces the possibility of mismatching pairs of different configurations or dimensions of the healing cap assemblies, because the bolt member 202 and the healing cap member 204 can be interlocked and packaged, transported and stored as a single unit.

Figure 12:
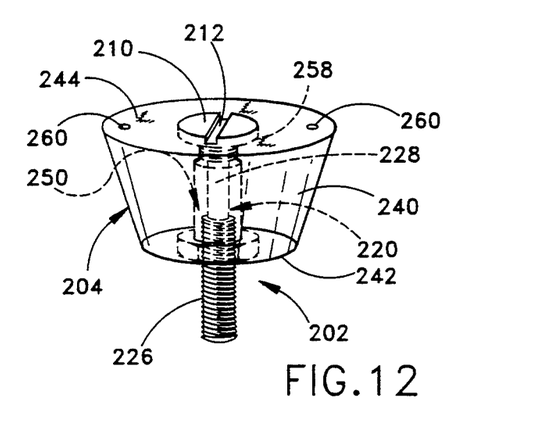
FIG. 12 is a perspective view showing the present invention interlockable elliptical healing cap assembly.

Referring to FIG. 12, there is shown a perspective view of the present invention interlockable elliptical healing cap assembly 200 as it is assembled in a patient's oral cavity. The disc shaped head segment 210 of the bolt member 202 is seated within the circular socket 258 at the larger distal end 244 of the healing cap member 204, so that the head segment 210 of the bolt member 202 is flush with the large distal end 244 of the healing cap member 204. The threaded proximal section 226 extends out from the small proximal end 242 of the healing cap member 204 for engagement with the dental implant fixture.

Figures 13, 14, 15:
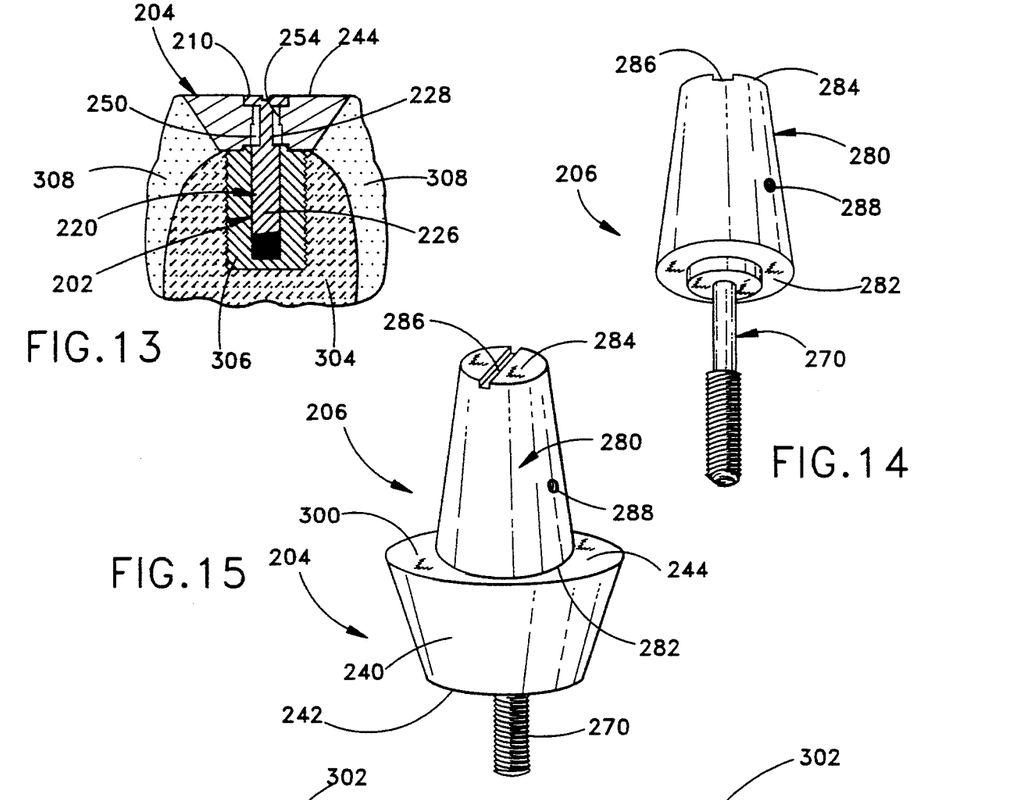
FIG. 13 is a cross-sectional view of the present invention anatomical restoration dental implant system, showing the elliptical healing cap member secured onto the implant fixture by the bolt member.
FIG. 14 is a perspective view of the present invention abutment member which matches the elliptical healing cap member of the present invention interlockable elliptical healing cap assembly.
FIG. 15 is a perspective view of the abutment member attached to the elliptical healing cap member of the present invention interlockable elliptical healing cap assembly.

FIG. 13 is a cross-sectional view of the present invention anatomical restoration dental implant system showing the elliptical healing cap member 204 secured onto a dental implant fixture 306 by the bolt member 202. It is noted that the shaft segment 220 of the bolt member 202 is longer than the interior bore 250 of the healing cap member 204, so that after the shaft segment 220 of the bolt member 202 extends through the interior bore 250 of the healing cap member 204, there is still a substantial portion of the threaded proximal section 226 of the shaft segment 220 of the bolt member 202, which can be threadedly engaged with the implant fixture 306 for fastening the healing cap member 204 to the exposed end of the implant fixture 306.

It is further noted that the outer diameter of the threaded proximal section 226 of the shaft segment 220 of the bolt member 202 is slightly smaller than the inner diameter of the smooth proximal section 252 of the interior bore 250 of the healing cap member 204, and the length of the distal section 228 of the shaft segment 220 of the bolt member 202 is longer than that of the distal section 254 of the interior bore 250 of the healing cap member 204. This feature ensures that after the proximal section 226 of the shaft segment 220 of the bolt member 202 is completely threaded through the distal section 254 of the interior bore 250 of the healing cap member 204, the healing cap member 204 and the bolt member 202 are no longer threadedly engaged.

This is another critical feature of the present invention. If the bolt member 202 is threadedly engaged with both the healing cap member 204 and the implant fixture 306, then the threaded relationship between the healing cap member 204 and the bolt member 202 will prevent the adjustment of the orientation of the healing cap member 204 when the bolt member 202 is tightened to the implant fixture 306 because of the threaded cross-engagement. When the bolt member 202 has a threaded relationship with the healing cap member 204 and is threadedly tightened into the implant fixture 306, it applies not only a translational downward force but also a rotational torque to the healing cap member 204. The translational force will act to fasten the healing cap member 204 to the implant fixture 306, but the rotational torque will act to rotate the healing cap member 204 about the implant fixture 306. This will destroy the desired orientation of the healing cap member 204, which is that the long-axis of the elliptical healing cap member 204 is aligned with the general radius direction of the patient's oral cavity. In the present invention, by having the bolt member 202 only threadedly engaged with the implant fixture 306, but not threadedly engaged with the healing cap member 204, when the healing cap assembly 200 is secured on the implant fixture 306, the desired orientation of the healing cap member can be maintained.

Referring to FIG. 14, there is shown a perspective view of a matching abutment member 206 of the present invention. The present invention abutment member 206 matches the elliptical healing cap member 204 of the present invention interlockable elliptical healing cap assembly 200. The abutment member 206 has a proximal bolt segment 270 which is identical to the bolt member 202 of the healing cap assembly 200. The abutment member 206 also has a frusto-conical shaped distal head segment 280. The frusto-conical shaped distal head segment 280 has a larger proximal end 282 integrally connected to the proximal bolt segment 270, and a smaller distal end 284 with a notch 286 to accommodate a driving tool such as a screw driver for rotating the abutment member 206. The frusto-conical shaped distal head segment 280 also has a side screw hole 288 to accommodate a small transverse screw for attaching a tooth analogue.

Referring to FIG. 15, there is shown a perspective view of the matching abutment member 206 attached to the elliptical healing cap member 204 of the interlockable elliptical healing cap assembly 200. Since the proximal bolt segment 270 of the abutment member 206 is identical to the bolt member 202 of the healing cap assembly 200, the abutment member 206 can simply replace the bolt member 202 when it is time to install a tooth analogue.

It is noted that the bolt segment 270 of the abutment member 206 is longer than the interior bore 250 of the healing cap member 204, so that after the bolt segment 270 of the abutment member 206 extends through the interior bore 250 of the healing cap member 204, there is still a substantial portion of a proximal section of the bolt segment 270 of the abutment member 206 which can be threadedly engaged with an implant fixture for fastening the healing cap member 204 thereupon.

It is further noted that the large circular proximal end 282 of the frusto-conical shaped distal head segment 280 of the abutment member 206 has a diameter smaller than the short-axis of the elliptical shaped distal end 244 of the healing cap member 204, so that when the abutment member 206 is fully secured on the healing cap member 204 in replacement of the bolt member 202 for supporting a tooth analogue, an elliptical shoulder 300 is created for matching the elliptical root of the tooth analogue.

This elliptical shoulder 300 is also a critical feature of the present invention. This solves the problem of mismatching between the root of the tooth analogue, which is often oval or elliptical, and the round or circular abutment shoulder provided by prior art dental implant systems. The smaller profile of the present invention elliptical shoulder 300 also allows two tooth analogues to be positioned at a desired or required close distance.

Figure 16:
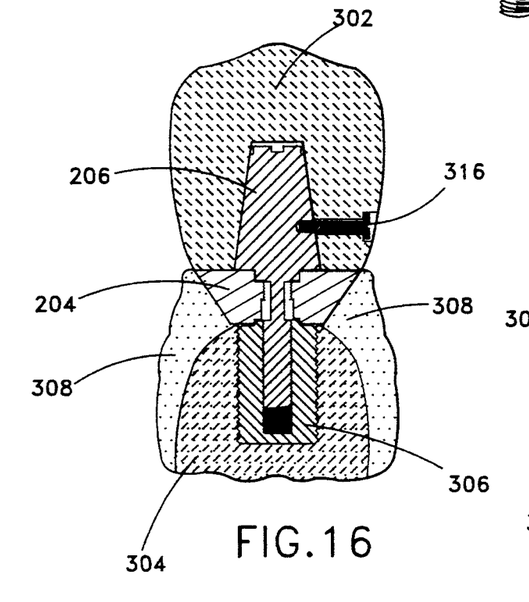
FIG. 16 is a cross-sectional view of the present invention anatomical restoration dental implant system, showing the matching abutment member which is secured on the elliptical healing cap member for supporting a tooth analogue.
Figure 17:
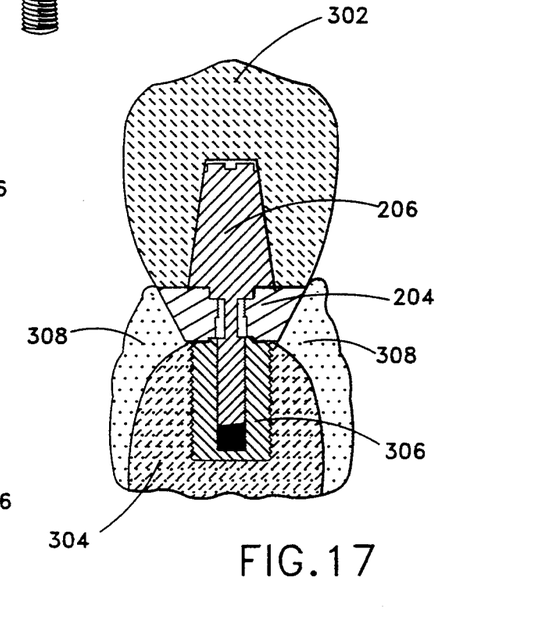
FIG. 17 is also a cross-sectional view of the present invention anatomical restoration dental implant system, observed at a 90 degree angle from that of FIG. 16, showing that no space is left between the tooth analogue and the gingival tissues because of the perfect matching between the elliptical root of the tooth analogue and the circular shoulder around the abutment.

Referring to FIGS. 16 and 17, there are shown that the matching abutment member 206 is secured on the elliptical healing cap member 204 for supporting a tooth analogue 302. FIG. 16 is a cross-sectional view of the present invention anatomical restoration dental implant system, whereas FIG. 17 is another cross-sectional view of the present invention anatomical restoration dental implant system, observed at a 90 degree angle from that of FIG. 16.

It can be seen than the oval shaped root of the tooth analogue 302 now matches perfectly with the elliptical shoulder 300 around the abutment member 206. As shown in FIGS. 16 and 17, the oval root of the tooth analogue 302 fully covers the elliptical shoulder 300. There are no longer two opposite narrow spaces left between the tooth analogue 302 and the gingival tissues 308. This solves the problem presented by prior art implant systems with circular abutment shoulders, shortens the period of time required for the gingival tissues 308 to recover and heal around the tooth analogue 302, and eliminates any possibility of having food debris and bacteria collected between the root of the tooth analogue 302 and the gingival tissues 308, which in turn expedites the complete healing of the gingival tissues 308 and reduces the chance of causing any infectious diseases.

Another problem solved by the present invention is the precise spacing between adjacent tooth analogues. In prior art dental implant systems the larger profile of the circular shaped shoulder often prevents two adjacent tooth analogues from being positioned at a desired close distance. This problem is solved by the present invention because the smaller profile of the elliptical shoulder 300 at the conjunction of the healing cap member 204 and the abutment member 206 at the direction perpendicular to the general radius direction of a patient's oral cavity allows two tooth analogues to be positioned at a closer distance.

It is also noted that the since the proximal bolt segment 270 of the abutment member 206 is exactly the same as the bolt member 202, the same interlockable and engagement relationship exists between the abutment member 206 and the healing cap 204. For example, when the abutment member 206 is threadedly engaged with the implant fixture 306, the healing cap member 204 and the abutment member 206 are no longer threadedly engaged.

Figure 18:
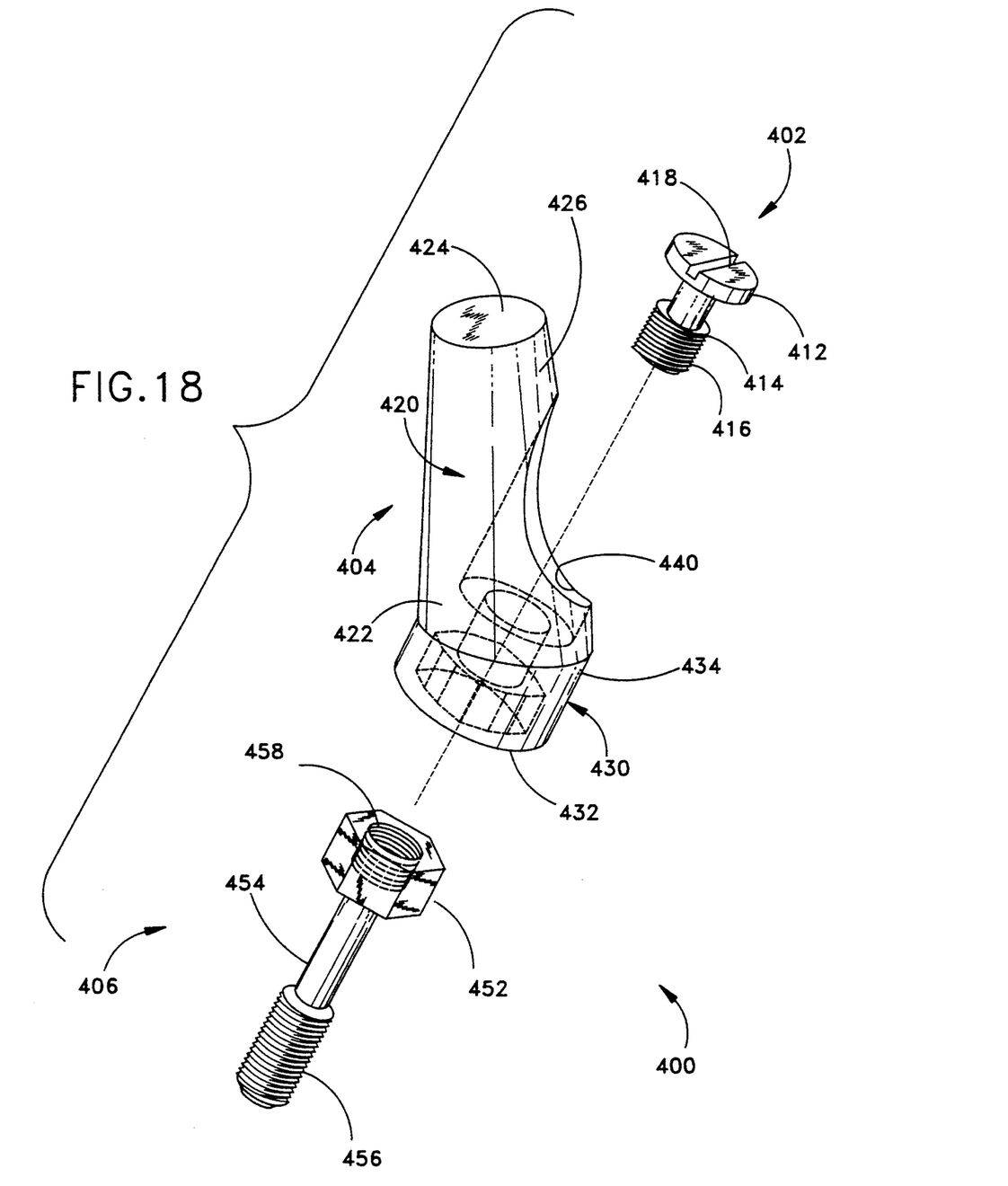
FIG. 18 is an exploded perspective view of the present invention angled abutment assembly, including an angled abutment member, a bolt member and a screw member.

Referring to FIG. 18, there is shown an exploded perspective view of the present invention angled abutment assembly 400, including a screw member 402, an angled abutment member 404, and a bolt member 406.

The screw member 402 has a disc-shaped widened head segment 412, a shaft segment 414 and a threaded segment 416. The widened head segment 412 has a top notch 418 to accommodate a driving tool such as a screw driver for rotating the screw member 402.

Referring now to FIGS. 18 through 21, the angled abutment member 404 has a frusto-conical shaped divergent portion 420 and a cylindrical shaped base portion 430 integrally connected together. The frusto-conical shaped divergent portion 420 has a larger proximal end 422, a smaller circular distal end 424, and a frusto-conical shaped sidewall 426. By way of example only, the diameter D1 of the larger proximal end 422 is between approximately 3 to 3½ mm, the diameter D2 of the smaller distal end 424 is between approximately 2 to 2½ mm, and the height H of the divergent portion 420 is between approximately 6 to 10 mm, preferably 8 mm.

The cylindrical shaped base portion 430 has a proximal end 432 and a distal end 434. The distal end 434 of the base portion 430 is integrally connected to the larger proximal end 422 of the divergent portion. The axis I of the divergent portion 420 is offset from the axis II of the base portion 430, which is perpendicular to the proximal end 432 of the base portion 430. By way of example, the offset angle A between axes I and II is between approximately 5 to 25 degrees.

The angled abutment member 404 has a stepped interior bore 440 extending from the proximal end 432 of the base portion 430 to the frusto-conical sidewall 426 of the divergent portion 420. The axis of the stepped interior bore 440 is perpendicular to the proximal end 432 of the base portion 430. The interior bore 440 has a wide cylindrical distal section 442, a narrow cylindrical middle section 444, and a wide polygonal proximal section 446. The polygonal proximal section 446 of the interior bore 440 is a twelve-side polygonal cavity.

Figures 19, 22:
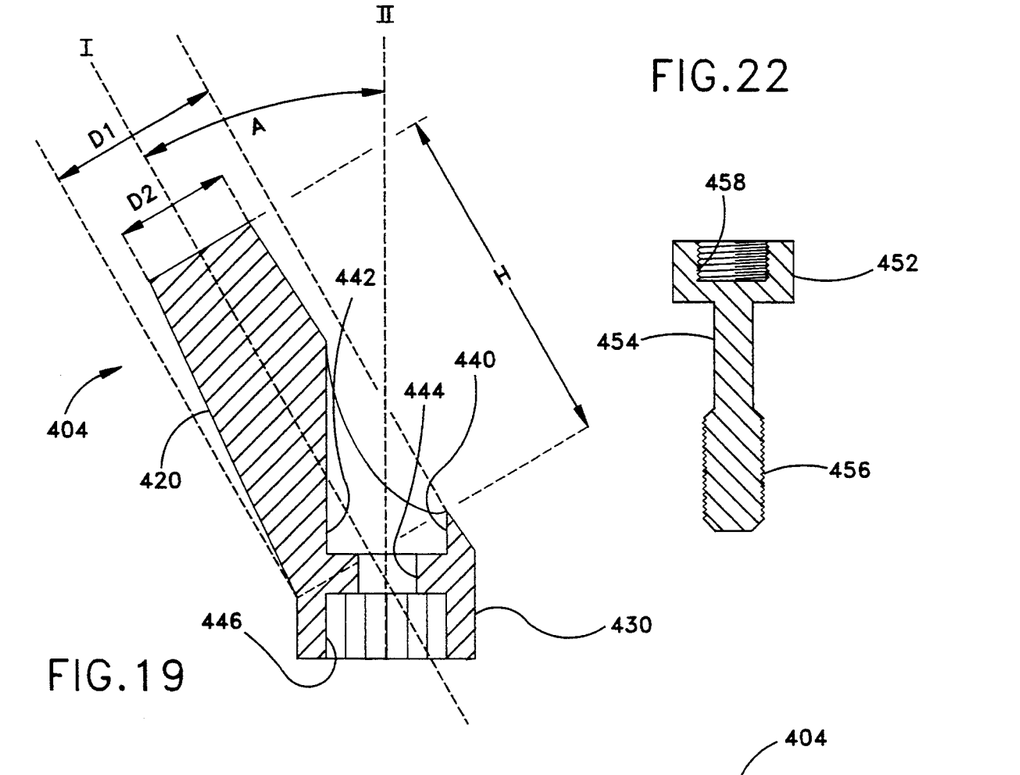
FIG. 19 is a cross-sectional view of the angled abutment member of the present invention angled abutment assembly.
FIG. 22 is a cross-sectional view showing the bolt member of the present invention angled abutment assembly.
Figure 20:
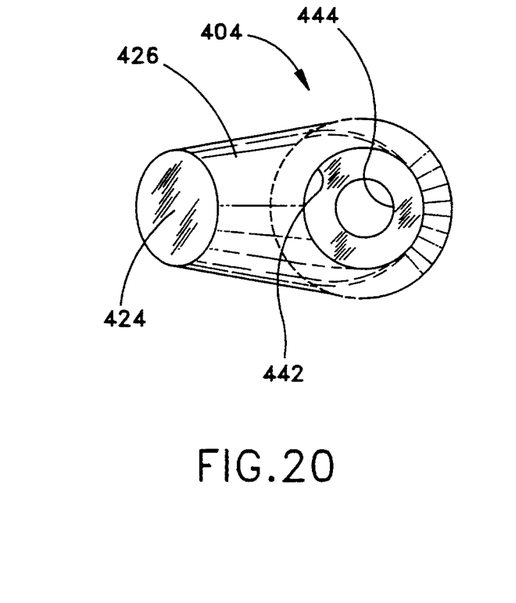
FIG. 20 is a top view of the angled abutment member of the present invention angled abutment assembly.
Figure 21:
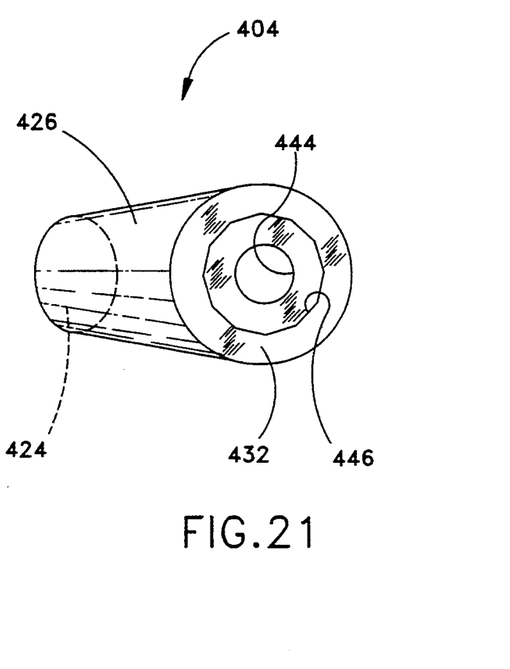
FIG. 21 is a bottom view of the angled abutment member of the present invention angled abutment assembly.

Referring to FIGS. 18 and 22, the bolt member 406 of the angled abutment assembly 400 is identical to the bolt member 202 of the healing cap assembly 200, except for the head segment 452. It has a hexagonal head segment 452, a thin shaft segment 454 and a thick threaded segment 456. The thin shaft segment 454 and a thick threaded segment 456 can interlockably engage with the healing cap 204 in the same fashion as the bolt member 202 of the healing cap assembly 200, as previously described. However, the head segment 452 of the bolt member 406 is now hexagonal shaped and has a top screw hole 458. This top screw hole is provided for mating with the threaded segment 416 of the screw member 402.

Figure 23:
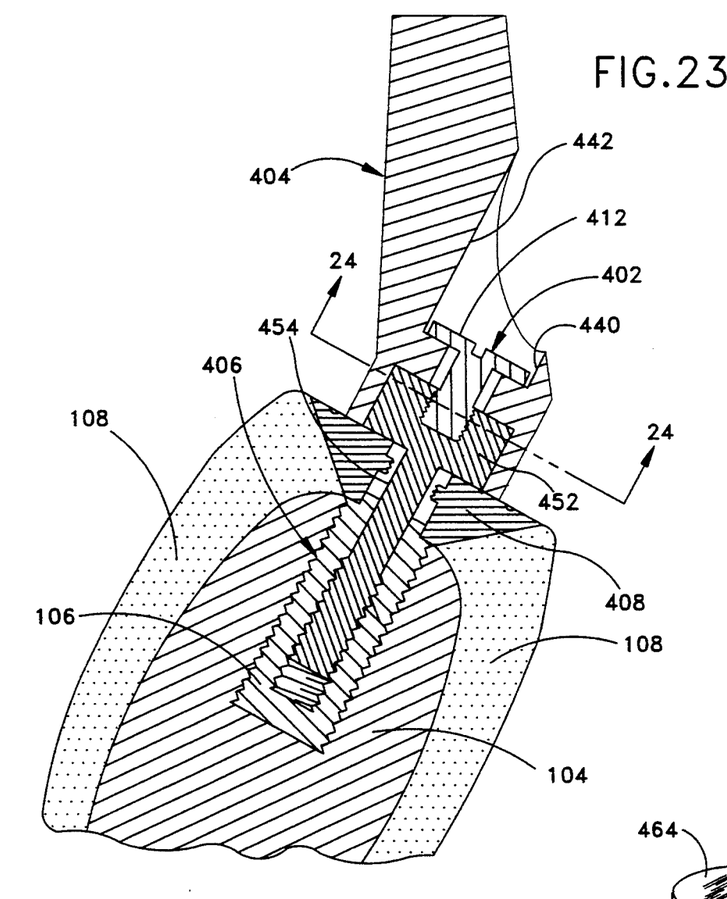
FIG. 23 is a cross-sectional view of the present invention anatomical restoration dental implant system, showing the angled abutment member secured on a healing cap for supporting a tooth analogue.

Referring to FIG. 23, there is shown a cross-sectional view of the present invention anatomical restoration dental implant system showing the angled abutment member 404 mounted on a healing cap 408, which is in turn mounted on the dental implant fixture 106, for supporting a tooth analogue (not shown). Implant fixture 106 is implanted in the patient's jaw bone 104, which is surrounded by gingival tissues 108.

Healing cap 408 is secured by the bolt member 406. It is noted that bolt member 406 can have an interlocked relationship before bolt member 406 is fully threaded into the implant 106. However, once bolt member 406 is fully threaded into the implant 106 as shown in FIG. 24, it is no longer engaged in any interlocked relationship with the healing cap 408, therefore allowing the angle of the healing cap to be adjusted to the best suitable position.

Angled abutment member 404 is mounted on the head segment 452 of the bolt member 406, and secured thereon by screw member 402. The widened head segment 412 of the screw member 402 is concealed within the widened cylindrical distal section 442 of the interior bore 440 of the angled abutment member 404.

Figure 24:
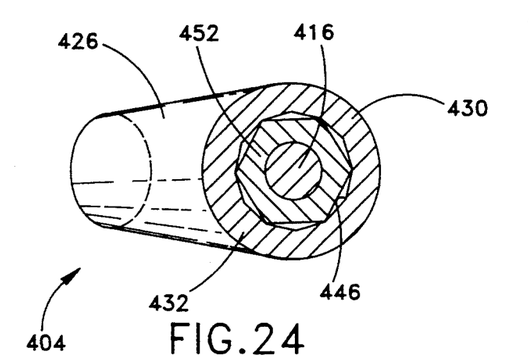
FIG. 24 is a cross-sectional view taken along line 24—24 of FIG. 23.

Referring to FIG. 24, the hexagonal shaped head segment 452 is fittedly engaged with the 12-side polygonal proximal section 446 of the interior bore 440 of the angled abutment member 404. This arrangement allows the angular orientation of the angled abutment member to be adjustable in any 30 degree interval. If the polygonal section 446 of the interior bore 440 of the angled abutment member 404 is also hexagonal shaped, then it only allows the angular orientation of the angled abutment member to be adjustable in 60 degree intervals.

Figure 25:
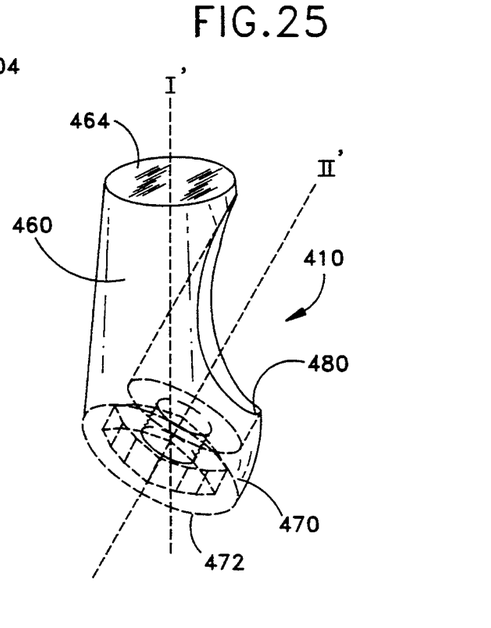
FIG. 25 is a perspective view of an alternative embodiment of the angled abutment member of the present invention angled abutment assembly.

It is noted that the external configuration of the present invention angled abutment member may also vary. Referring to FIG. 25, there is shown an alternative embodiment of the angled abutment member of the present invention angled abutment assembly. The alternative embodiment of the angled abutment member 410 still has a frusto-conical shaped divergent portion 460 and a base portion 470. However, the base portion 470 is no longer cylindrical shaped, but rather merges with the larger proximal end of the divergent portion 460. In fact, the angled abutment member 410 can be perceived as having a continuous divergent body with a smaller distal end 464 and a larger proximal end 472. The characteristic of this continuous divergent body is that its distal end 464 is not parallel to its proximal end 472, and its interior bore 480 is perpendicular to its proximal end 472. In other words, the axis II' of the interior bore 480 is offset from the axis I' of the divergent body 460. The angle between axes I' and II' is again preferably between approximately 5 degrees to 25 degrees.

Defined in detail, the present invention is an anatomical restoration dental implant system implantable in the gingival tissue and the alveolus of the jaw bone, comprising:

(a) a dental implant fixture having proximal and distal end portions, the proximal end portion having means for being embedded in opened gingival tissue and the alveolus of the jaw bone, the distal end portion having an exposed end being accessible from the outer surface of the jaw bone, the fixture being made of a substance permitting healing of the opened gingival tissue and growth of the jaw bone about the fixture, the fixture further including a hollow extending along an axis of the fixture from an opening in the distal end portion towards the proximal end portion, the hollow having threads along at least a portion of its length;

(b) means for sealing the hollow of the implant fixture during a period after implantation in which the jaw bone is growing about the proximal portion of the implant fixture;

(c) healing cap means for providing a predetermined oval contour to the gingival tissue adjacent the distal end of the implant fixture, such that the gingival tissue re-heals in an oval contour reverse to that of the contour of the healing cap means;

(d) a tooth analogue;

(e) angled abutment means for supporting the tooth analogue along a direction offset from the axis of the fixture;

(f) means for securing the tooth analogue to the angled abutment means;

(g) the abutment means being an angled assembly, including:

(i) a screw member having a widened head segment, a shaft segment and a threaded segment;

(ii) an angled abutment member having a frusto-conical shaped divergent portion and a cylindrical shaped base portion, the divergent portion having a larger proximal end, a smaller circular distal end, and a frusto-conical shaped sidewall, the base portion having a circular proximal end and a distal end, the distal end of the base portion integrally connected to the larger proximal end of the divergent portion, the angled abutment member further having a stepped interior bore extending from the proximal end of the base portion to the frusto-conical sidewall of the divergent portion, along an axis perpendicular to the proximal end of the base portion and offset from an axis of the divergent portion, the interior bore having a wide cylindrical distal section, a narrow cylindrical middle section, and a wide 12-side polygonal proximal section; and (iii) a bolt member having a hexagonal head segment, an elongated narrow shaft segment and a widened threaded segment, the head segment having a top screw hole, the bolt member and the healing cap being interlockable before the threaded segment of the bolt member is fully threaded into the implant fixture;

(h) whereby the bolt member can be used to secure the healing cap to the implant fixture by threading the threaded segment of the bolt member into the hollow of the implant fixture, the angled abutment member can be mounted on the healing cap by engaging the head segment of the bolt member with the 12-side polygonal distal section of the interior bore of the angled abutment member, which allows the angular orientation of the angled abutment member to be adjustable in any 30 degree interval, and the screw member can be used to secure the angled abutment member to the bolt member by threading the threaded segment of the screw member into the top screw hole of the head segment of the bolt member, where the head segment of the screw member is concealed within the wide cylindrical distal section of the interior bore of the angled abutment member.

Defined broadly, the present invention is an angled abutment assembly attachable to a healing cap mounted on an anatomical restoration dental implant fixture, which is embedded into a patient's jawbone and has an exposed end having a hollow portion with inner screw threads, for supporting a tooth analogue along a direction offset from an axis of the fixture, the angled abutment assembly comprising: (a) a screw member having a widened head segment and a shaft segment with a threaded proximal section; (b) an angled abutment member having a distal divergent portion and a proximal base portion integrally connected together, the divergent portion having a smaller distal end, the base portion having a larger proximal end, the angled abutment member further having an interior bore extending from the proximal end of the base portion to the divergent portion along an axis perpendicular to the proximal end of the base portion and offset from an axis of the divergent portion, the interior bore having a narrow cylindrical distal section, and a wide polygonal proximal section; and (c) a bolt member having a hexagonal head segment and an elongated shaft segment with a threaded proximal section, the head segment having a top screw hole; (d) whereby the bolt member can be used to secure the healing cap to the implant fixture, the angled abutment member can be mounted on the healing cap by engaging the head segment of the bolt member with the polygonal distal section of the interior bore of the angled abutment member, which allows the angular orientation of the angled abutment member to be adjustable, and the screw member can be used to secure the angled abutment member to the bolt member.

Defined alternatively, the present invention is a method for supporting a tooth analogue along a direction offset from an axis of a dental fixture implanted in the gingival tissue and the alveolus of the jawbone in a patient's oral cavity, the method comprising the steps of: (a) implanting a fixture having proximal and distal end portions, the proximal end portion having means for being embedded in opened gingival tissue and the alveolus of the jaw bone, the distal end portion being accessible from the outer surface of the jaw bone, the fixture being made of a substance permitting healing of the opened gingival tissue and growth of the jaw bone about the fixture, the fixture further including a hollow extending from the distal end portion toward the proximal end portion, the hollow being threaded along at least a portion of its length; (b) securing a healing cap to the distal end of the implant fixture by using a bolt member, the bolt member having a hexagonal head segment with a top screw hole and an elongated shaft segment with a threaded proximal section which is threaded into the hollow of the implant fixture; (c)

providing an abutment member which has a distal divergent portion and a proximal base portion integrally connected together, the divergent portion having a smaller distal end, the base portion having a larger proximal end, the angled abutment member further having an interior bore extending from the proximal end of the base portion to the divergent portion along an axis perpendicular to the proximal end of the base portion and offset from an axis of the divergent portion, the interior bore having a narrow cylindrical distal section and a wide polygonal proximal section; (d) placing the angled abutment member on the healing cap by engaging the head segment of the bolt member with the polygonal distal section of the interior bore of the angled abutment member, which allows the angular orientation of the angled abutment member to be adjustable; (e) securing the angled abutment member to the bolt member by using a screw member which is engageable to the top screw hole of the head segment of the bolt member; and (f) releasibly attaching a tooth analogue to the divergent portion of the angled abutment member such that the tooth is supported along a direction offset from the axis of the fixture.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. An anatomical restoration dental implant system implantable in the gingival tissue and the alveolus of the jaw bone, comprising:
    a. a dental implant fixture having proximal and distal end portions, the proximal end portion having means for being embedded in opened gingival tissue and the alveolus of the jaw bone, the distal end portion having an exposed end being accessible from the outer surface of the jaw bone, the fixture being made of a substance permitting healing of the opened gingival tissue and growth of the jaw bone about the fixture, the fixture further including a hollow extending along an axis of the fixture from an opening in the distal end portion towards the proximal end portion, the hollow having threads along at least a portion of its length;
    b. means for sealing the hollow of the implant fixture during a period after implantation in which the jaw bone is growing about the proximal portion of the implant fixture;
    c. healing cap means for providing a predetermined oval contour to the gingival tissue adjacent the distal end of the implant fixture, such that the gingival tissue re-heals and conforms to the contour of the healing cap means;
    d. a tooth analogue;
    e. angled abutment means for supporting the tooth analogue along a direction offset from said axis of said fixture;
    f. means for securing said tooth analogue to said angled abutment means;
    g. said angled abutment means including:
        (i) a screw member having a widened head segment, a shaft segment and a threaded segment;
        (ii) an angled abutment member having a frusto-conical shaped divergent portion and a cylindrical shaped base portion, the divergent portion having a larger proximal end, a smaller circular distal end, and a frusto-conical shaped sidewall, the base portion having a circular proximal end and a distal end, the distal end of the base portion integrally connected to the larger proximal end of the divergent portion, the angled abutment member further having a stepped interior bore extending from the proximal end of the base portion to the frusto-conical sidewall of the divergent portion, along an axis perpendicular to the proximal end of the base portion and offset from an axis of the divergent portion, the interior bore having a wide cylindrical distal section, a narrow cylindrical middle section, and a wide 12-side polygonal proximal section; and
        (iii) a bolt member having a hexagonal head segment, an elongated narrow shaft segment and a widened threaded segment, the head segment having a top screw hole, the bolt member and said healing cap being interlockable before the threaded segment of the bolt member is fully threaded into said implant fixture;
    h. whereby said bolt member can be used to secure said healing cap to said implant fixture by threading said threaded segment of said bolt member into said hollow of said implant fixture, said angled abutment member can be mounted on said healing cap by engaging said head segment of said bolt member with said 12-side polygonal proximal section of said interior bore of said angled abutment member, which allows the angular orientation of said angled abutment member to be adjustable in any 30 degree interval, and said screw member can be used to secure said angled abutment member to said bolt member by threading said threaded segment of said screw member into said top screw hole of said head segment of said bolt member, where said head segment of said screw member is concealed within said wide cylindrical distal section of said interior bore of said angled abutment member.

2. The invention as defined in claim 1 wherein said head segment of said screw member is circular disc shaped.

3. The invention as defined in claim 1 wherein said head segment of said screw member is hexagonal shaped.

4. The invention as defined in claim 1 wherein said head segment of said screw member has means cooperable with a driving tool.

5. The invention as defined in claim 4 wherein said means cooperable with said driving tool is a top notch on said head segment of said screw member.

6. An angled abutment assembly attachable to a healing cap mounted on an anatomical restoration dental implant fixture, which is embedded into a patient's jaw bone and has an exposed end having a hollow portion with inner screw threads, for supporting a tooth analogue along a direction offset from an axis of the fixture, the angled abutment assembly comprising:

a. a screw member having a widened head segment, and a shaft segment with a threaded proximal section;

b. an angled abutment member having a distal divergent portion and a proximal base portion integrally connected together, the divergent portion having a smaller distal end, the base portion having a larger proximal end, the angled abutment member further having an interior bore extending from the proximal end of the base portion to the divergent portion along an axis perpendicular to the proximal end of the base portion and offset from an axis of the divergent portion, the interior bore having a narrow cylindrical distal section and a wide polygonal proximal section; and     c. a bolt member having a hexagonal head segment and an elongated shaft segment with a threaded proximal section, the head segment having a top screw hole, the hexagonal head segment being engaged with said polygonal distal section of said interior bore of said angled abutment member which allows adjustment of the angular orientation of said angled abutment member but acts to prevent any rotation of said angled abutment member after its angular orientation is adjusted;

d. whereby said bolt member can be used to secure said healing cap to said implant fixture, and said screw member can be used to secure said angled abutment member to said bolt member.

7. The invention as defined in claim 6 wherein said head segment of said screw member is circular disc shaped.

8. The invention as defined in claim 6 wherein said head segment of said screw member is hexagonal shaped.

9. The invention as defined in claim 6 wherein said head segment of said screw member has means cooperable with a driving tool.

10. The invention as defined in claim 9 wherein said means cooperable with said driving tool is a top notch on said head segment of said screw member.

11. The invention as defined in claim 6 wherein said cylindrical distal section of said interior bore of said angled abutment member further comprises a widened socket for receiving said widened head segment of said screw member.

12. A method for supporting a tooth analogue along a direction offset from an axis of a dental fixture implanted in the gingival tissue and the alveolus of the jawbone in a patient's oral cavity, the method comprising the steps of:

a. implanting a fixture having proximal and distal end portions, the proximal end portion having means for being embedded in opened gingival tissue and the alveolus of the jaw bone, the distal end portion being accessible from the outer surface of the jaw bone, the fixture being made of a substance permitting healing of the opened gingival tissue and growth of the jaw bone about the fixture, the fixture further including a hollow extending from the distal end portion toward the proximal end portion, the hollow being threaded along at least a portion of its length;

b. securing a healing cap to said distal end portion of said implanted fixture by using a bolt member, the bolt member having a hexagonal head segment with a top screw hole and an elongated shaft segment with a threaded proximal section which is threaded into said hollow of said fixture;

c. providing an angled abutment member which has a distal divergent portion and a proximal base portion integrally connected together, the divergent portion having a smaller distal end, the base portion having a larger proximal end, the angled abutment member further having an interior bore extending from the proximal end of the base portion to the divergent portion along an axis perpendicular to the proximal end of the base portion and offset from an axis of the divergent portion, the interior bore having a narrow cylindrical distal section and a wide polygonal proximal section;

d. placing said angled abutment member on said healing cap and adjusting the angular orientation of said angled abutment member, engaging said head segment of said bolt member with said polygonal proximal section of said interior bore of said angled abutment member to prevent any rotation of said angled abutment member;

e. securing said angled abutment member to said bolt member by using a screw member which is engageable to said top screw hole of said head segment of said bolt member; and     f. releasibly attaching a tooth analogue to said divergent portion of said angled abutment member such that said tooth analogue is supported along a direction offset from said axis of said fixture.

13. The invention as defined in claim 12 further comprising the step of making said polygonal proximal section of said interior bore of said angled abutment member a 12-side polygonal cavity so that when said hexagonal head segment of said bolt member is engaged therein, the angular orientation of said angled abutment member can be adjusted in any 30 degree interval.

\* \* \* \* \*